United States Patent [19]

Martens et al.

[11] Patent Number: 5,363,854

[45] Date of Patent: Nov. 15, 1994

[54] METHOD OF DETECTING ANOMALIES OF THE SKIN, MORE PARTICULARLY MELANOMAE, AND APPARATUS FOR CARRYING OUT THE METHOD

[75] Inventors: Gerhard Martens, Henstedt-Ulzburg; Erhard P. H. Günzel, Westerwalsede, both of Germany

[73] Assignee: U.S. Philips Corporation, New York, N.Y.

[21] Appl. No.: 745,023

[22] Filed: Aug. 14, 1991

[30] Foreign Application Priority Data

Aug. 24, 1990 [DE] Germany ............... 4026821

[51] Int. Cl.$^5$ ............................ A61B 6/00
[52] U.S. Cl. .................... 128/665; 356/390
[58] Field of Search .......... 128/664, 665, 633; 356/317, 318, 390, 417–420; 250/461.1, 461.2, 459.1

[56] References Cited

U.S. PATENT DOCUMENTS

| | | | |
|---|---|---|---|
| 3,335,716 | 8/1967 | Alt et al. | 128/664 |
| 4,236,082 | 11/1980 | Butler | 250/461 |
| 4,505,583 | 3/1985 | Konomi . | |
| 4,556,057 | 12/1985 | Hiruma et al. | 128/665 |
| 4,773,097 | 9/1988 | Suzaki et al. | 382/6 |
| 4,821,117 | 4/1989 | Sekiguchi | 358/98 |
| 5,003,977 | 4/1991 | Suzuki et al. | 128/633 |
| 5,097,135 | 3/1992 | Mikano et al. | 250/461.1 |

FOREIGN PATENT DOCUMENTS

| | | |
|---|---|---|
| 0003015 | 1/1978 | European Pat. Off. . |
| 221556 | 4/1985 | German Dem. Rep. . |
| WO88/09145 | 12/1988 | Germany . |

*Primary Examiner*—Angela D. Sykes
*Attorney, Agent, or Firm*—Jack D. Slobod

[57] ABSTRACT

An apparatus for detecting anomalies of the skin, more particularly melanomae, includes a light source for illuminating a two-dimensionally extending examination region of the skin, successively, with ultraviolet light range and with visible light. A camera records a fluorescence picture of the examination region having signal values F(x,y) at its picture points x,y in response to the illumination with ultraviolet light and a reference picture having signal values R(x,y) at its picture points x,y in response to the illumination with visible light. A memory stores the signal values of at least one of the fluorescence picture and said reference picture, and a processor responsive to the memory produces an output picture having respective signal values A(x,y) at its picture points x,y which are formed from respective quotients F(x,y)/R(x,y) of the signal values of the fluorescence and reference pictures at the same picture points. Various filters are provided positioned or positionable between the light source and the examination region or in front of the camera.

21 Claims, 1 Drawing Sheet

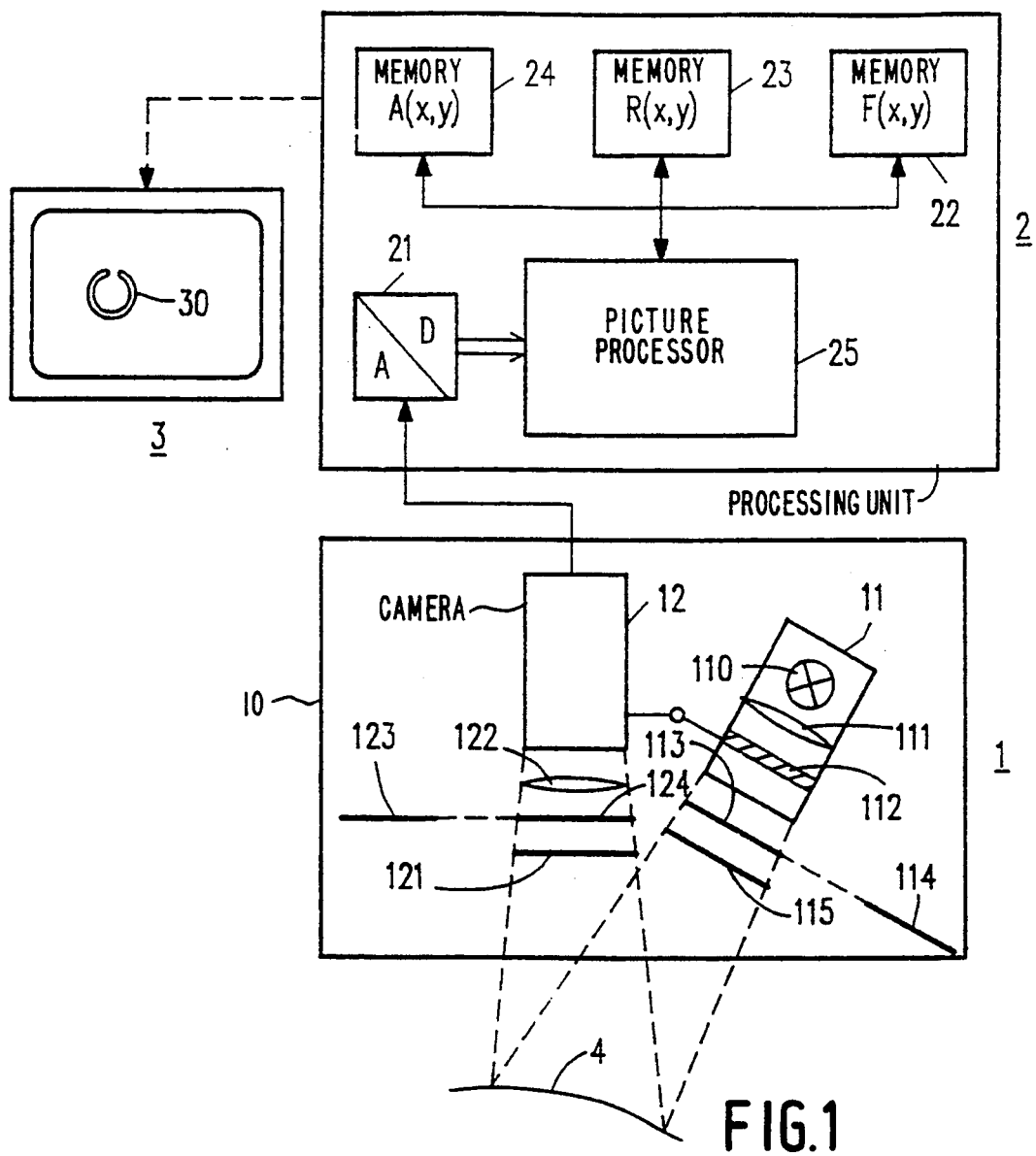
FIG.1
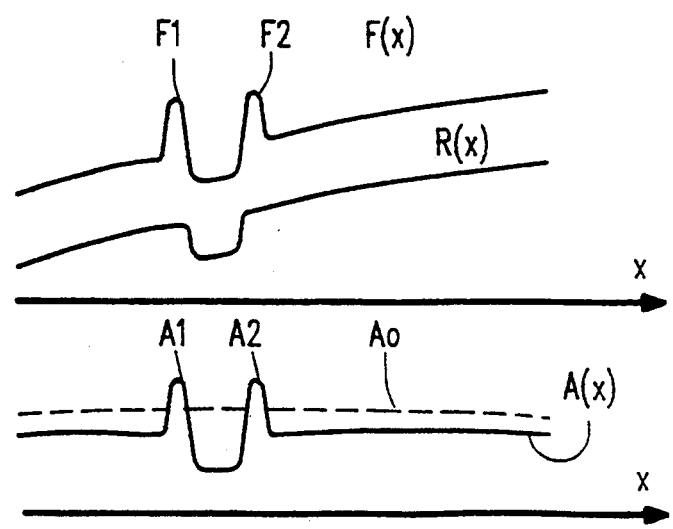
FIG.2a
FIG.2b

METHOD OF DETECTING ANOMALIES OF THE SKIN, MORE PARTICULARLY MELANOMAE, AND APPARATUS FOR CARRYING OUT THE METHOD

FIELD OF THE INVENTION

The invention relates to a method of detecting anomalies of the skin, more particularly melanomae, in which the fluorescence light produced by illumination with light from a first wavelength range is evaluated, and to an apparatus for carrying out this method.

BACKGROUND OF THE INVENTION

Such a method and such an arrangement are known from DE-PS 37 18 202. In the known apparatus, by means of a spectral photometer the back-scattered light is recorded and the intensities of the reflected light and of the fluorescence light are determined. Since the fluorescence light is particularly intense in the transitional region between the melanoma and the sound tissue, there can be derived from the spectrum thus determined by means of an empirically determined stored table whether or not an anomaly is present in the region of the tissue surface each time recorded by the spectral photometer.

Melanomae are irregularly formed and irregularly pigmented lesions of the skin, which are externally very similar to a birth-mark (nevus). Some patients have on their whole body surface a comparatively large number of birth-marks. If by means of the known method it should be examined whether in fact only birth-marks and not melanomae are concerned, the spectral photometer should be brought into a plurality of positions with respect to the patient to be examined and the intensities determined by the spectral photometer should be evaluated. Such an examination would be very time-consuming.

SUMMARY OF THE INVENTION

The present invention has for its object to carry out a method of the kind mentioned in the opening paragraph in such a manner that the examination of an extensive region can take place comparatively rapidly.

Starting from an apparatus for carrying out this method, this object is achieved in that a two-dimensionally extending examination region is illuminated with light of the first wavelength range and a fluorescence picture of the examination region is recorded, in that the examination region is illuminated with light of a second wavelength and a reference picture is recorded in the second wavelength range, and in that by standardization of the fluorescence picture on the reference picture an output picture is produced. As "fluorescence picture" the image of the examination region in a wavelength range is designated which comprises greater wavelengths than the first wavelength range.

Therefore, whereas in the known method an evaluation of the spectral variation of the back-scattered light takes place, which of course can occur always only for a small region of the skin, according to the invention an evaluation of the spatial variation of the intensity—in an extensive region (i.e. a region of 50 mm×50 mm or larger)—takes place preferably in the wavelength range in which the fluorescence has its maximum. As a result, several lesions or birth-marks on a large skin surface (for example the back) can be examined simultaneously.

The evaluation of the fluorescence picture alone is not yet sufficiently reliable because also the topology of the skin surface in the examination region has a very strong influence on the intensity distribution of the fluorescence picture. An intensity maximum in the fluorescence picture is therefore not yet an unambiguous indication with respect to the presence of an anomaly because the intensity increase in the fluorescence picture around an anomaly can be smaller than the intensity variation brought about by the topology and other influences.

Therefore, according to the invention, a reference picture is produced. The reference picture is a picture which is independent at least to a great extent on the intensity differences of the fluorescence, but is subjected to all the other influences, which also act upon the fluorescence picture. Therefore, if an output picture is produced by standardization of the fluorescence picture on the reference picture, in this output picture the last-mentioned influences are eliminated practically completely. A sound skin surface is therefore imaged in this output picture with a substantially uniform brightness, while the environmental region of a melanoma having a width of about 10 mm has in the output picture an increased intensity.

It should be noted here that from U.S. Pat. No. 4,236,082 an identification method is known, in which the hand of a human being is irradiated for a short time by a U.V. light source and in which a camera records a fluorescence picture of the hand. By means of this method, the contrast of fine structures of the hand, for example of the hand lines, should be enlarged.

An apparatus for carrying out the method according to the invention is characterized by at least one light source for illuminating the examination region with light in a first and in a second wavelength range, a camera that can be aligned with respect to the examination region for recording the fluorescence picture and the reference picture and for producing corresponding electrical signals, a memory arrangement for storing at least one picture and a processing unit for producing an output picture in dependence upon the quotient of the signal values of the fluorescence picture and of the reference picture assigned to the same picture points.

Since the second wavelength range as a rule does not coincide with the first wavelength range, the illumination required for recording the fluorescence picture and the reference picture can be obtained by means of two light sources, which each emit one of the two wavelength ranges. Since, however, the reference picture must depend, but for the fluorescence having different intensities, upon the same factors as the fluorescence picture, the light sources must have the same position and moreover the same directional characteristic when recording the pictures. A more favourable solution on the contrary is characterized by at least one light source emitting both in the first and in the second wavelength range, a first filter for transmitting light from the first wavelength range and for suppressing light having the wavelength of the fluorescence light and a second filter for transmitting the second wavelength range, while each time one of the two filters can be arranged in the beam path between the light source and the examination region.

In this embodiment of the invention, only one light source is present so that with both pictures the same position between the light source and the examination region, the same directional characteristic etc. are guaranteed. Since solely the two filters in the beam path must be exchanged, the fluorescence picture and the reference picture can be produced at a small relative time distance so that movement artefacts are avoided to a great extent. It is also possible to use several light sources, which emit light in both wavelengths and are preferably uniformly distributed around the camera and illuminate uniformly the examination region.

A further embodiment of the invention is characterized by a frosted pane present in the beam path of the light source. As a result, a symmetrical radiation characteristic and a uniform illumination of the examination region are obtained.

A further embodiment of the invention comprises a filter that can be arranged before the camera for transmitting light from the second wavelength range. This filter present in the beam path of the camera when recording the reference picture suppresses light from the first wavelength range and attenuates any environmental light so that there can also be worked in an examination room which is not completely darkened. As the case may be, the second wavelength range and the wavelength range of the fluorescence light may coincide; in this case, the filter may also remain in the beam path when recording the fluorescence picture.

In a further embodiment of the invention, polarization filters are provided, which can be introduced into the beam path in front of the camera and the light source and are shaped and arranged so that the directed reflection in the picture produced by the camera is suppressed. The polarisation filters are used when recording the reference picture and suppress the directed reflection (lustre reflection). The reference picture therefore is only a scattered picture of the examination region.

BRIEF DESCRIPTION OF THE DRAWINGS

The invention will now be described more fully with reference to the accompanying drawing, in which:

FIG. 1 shows an apparatus for carrying out the method according to the invention, FIG. 2a shows a brightness profile in the fluorescence picture and in the reference picture for the same profile line, and FIG. 2b shows the associated profile in the output picture.

DESCRIPTION OF THE PREFERRED EMBODIMENT

The apparatus shown in FIG. 1 comprises an image-sensing device 1, a picture processing unit 2 and a picture display unit 3. The image-sensing unit 1 produces of an examination region 4 (the skin of a patient) fluorescence pictures and reference pictures, which are processed by the picture processing unit 2 to an output picture, which can be displayed on the picture display unit 3.

The image sensor device comprises a housing or a holding device 10, which is arranged so as to be movable and pivotable in a stand (not shown). The housing or the holding device accommodates an illumination device 11 and a video camera 12 in a defined position with respect to each other and to the housing. The illumination device 11 illuminates the examination region 4 during recording of a fluorescence picture with ultraviolet light in a wavelength range of 340 to 380 nm. When recording a reference picture, blue light is produced in a wavelength range around 435 nm and the light transmission for the ultraviolet light is blocked.

The illumination device comprises a light source 110, which can produce light in a wavelength range which includes the above ranges. Suitable light sources are, for example, metal halogen ultraviolet lamps or UVA phosphor tubes, as are used in upper-body or whole-body tanning apparatuses. After an optical projection system 111, the light produced by the light source traverses a frosted pane 112, which brings about a symmetrical radiation distribution or a uniform illumination of the examination region.

The illumination device 11 further comprises two filters 113 and 114, of which one is present in the beam path behind the frosted pane 112 and which can be coupled to each other through a filter exchange device. The filter 113, which is present in the beam path when producing a reference picture, suppresses ultraviolet light and transmits visible light. On the contrary, the filter 114 transmits ultraviolet light and suppresses light at least in the fluorescence wavelength range (450 to 490 nm).

Moreover, when recording a reference picture, further a polarization filter 115 is present in the beam path of the illumination device 11, which in conjunction with a corresponding polarization filter 121 before the camera 12 suppresses the directed reflection or the lustre reflection. Preferably, the filters 113 and 115 are accommodated in a common holder. A few polarization filters are substantially impervious to ultraviolet light. In these cases, the UV suppression filter 113 may be dispensed with; the polarization filter 115 must then be removed from the beam path, however, when recording a fluorescence picture.

In front of the camera 12, which produces an electrical video signal linearly dependent upon the brightness at the different picture points, which corresponds to the picture on its photosensitive surface, a camera objective 122 is arranged, which projects the examination region 4 onto the photosensitive surface of the camera. Moreover, two filters 123 and 124 are provided, of which one is present in the beam path. The filter 124 has a narrow transmission range around about 435 nm, while the filter 123 has a transmission range of 450 to 490 nm. As indicated by a broken line, the filter can be exchanged by means of a filter exchange device. The polarization filter 121 is preferably also mounted in the holder 124.

The output signal of the camera 12 is supplied to an analog-to-digital converter 21, which is contained in the picture processing unit 2 and produces from this signal a sequence of digital data words, which represent the brightness at a picture point of the picture recorded by the camera 12. The picture processing unit 2 comprises three picture memories 22, 23 and 24 and a picture processor 25.

When recording a fluorescence picture, solely the filter 114 is present in the beam path of the light source 11 and this filter transmits ultraviolet light and suppresses visible light. The filter 123 transmitting the fluorescence light is present in the beam path of the camera. The transmission ranges of the filter 114 and 123 operative when recording a fluorescence picture are tuned to each other in such a manner that a maximum fluorescence is obtained in the fluorescence wavelength range. Upon an excitation by ultraviolet light in the range between 340 and 380 nm, the wavelength range with a maximum output of fluorescence radiation lies between 450 and 490 nm (blue).

The video signal produced when recording the fluorescence picture is supplied through the picture processor 25 to the picture memory 22. Corrections are further carried out, for example the dark currents of the television camera are compensated, etc. The values $F(x,y)$ contained in the digital picture memory 22 therefore represent the intensity of the fluorescence light at the different picture points of the two-dimensional examination region 4. For reducing the noise, the picture signals obtained during several picture periods can be added or averaged in the memory 22.

In FIG. 2a, the intensity profile $F(x)$ along a line passing through a melanoma in the x direction is designated by $F(x)$. The profile $F(x)$ shows two relative intensity maxima F1, F2, which are to be assigned to a transitional region around the melanoma having a width of a few millimeters. In this region, an increased fluorescence intensity is obtained. Since the fluorescence intensity is not constant, however, over the remaining sound surfaces—for example because the individual zones of the examination region have a different inclination to the illumination device 11 and therefore are illuminated with different intensities—, there are values $F(x)$, which correspond to an even higher fluorescence intensity. For this reason, it is not possible without further expedients to determine in the fluorescence picture the relative intensity maxima and thus to identify a pigment birthmark of the skin unambiguously as a melanoma.

Therefore, a further reference picture is produced. The reference picture should be subjected to the same influences as the fluorescence picture, but the increased fluorescence activity at the edge of the melanoma should not appear in the reference picture. The wavelength ranges, in which the examination region 4 is illuminated and in which the reference picture is recorded, then correspond to each other. In the embodiment, a wavelength range around 435 nm was chosen. However, this range may also be chosen so that it corresponds to the fluorescence wavelength range (450 to 490 nm) in case the illumination device in this range has a sufficient intensity. In this case, the filter 124 may be dispensed with and the filter 123 may be permanently present in the beam path of the camera. However, it is also possible to record the reference picture at even higher wavelengths. Preferably, as wavelength range for the reference picture one of the so-called isobestic wavelength ranges is chosen. These ranges are the ranges in which blood rich in oxygen and blood poor in oxygen show the same absorption. The reference picture is then independent of the oxygen saturation degree of the blood, which determines to a considerable extent the colouring of the tissue. Such wavelength ranges lie inter alia at about 550 nm or at 585 nm; in these ranges, the ultraviolet light source 110 shows pronounced (mercury) emission lines.

The electrical signal corresponding to the reference picture is also digitized by the analog-to-digital converter 21, but is stored by the picture processor—as the case may be while carrying out suitable correction algorithms—in the memory 23. The latter therefore contains digital values $R(x,y)$, which correspond to the brightness at the individual points of the examination region.

FIG. 2a shows the variation $R(x)$ of the intensity profile for the same line as the intensity profile $F(x)$ in the fluorescence picture. It can be seen that the signal $R(x)$ has a variation corresponding to that of the signal $F(x)$ if once the relative maxima F1, F2 are left out of consideration, which have no correspondence in the profile $R(x)$. These conformities originate from the fact that the examination region were illuminated and recorded with both pictures from the same perspective. If it is further ensured that the pictures are produced at a close relative time distance, which is possible without the use of further means, because only filters in the beam path need be exchanged, also the artefacts are avoided, which are produced by movements of the patient in the time interval between the instants of recording the pictures.

After the fluorescence picture and the reference picture have been stored in this manner in the picture memories 22 and 23, an output picture $A(x,y)$ is derived from the stored values, in that $F(x,y)$ is standardized on $R(x,y)$. For this purpose, the quotient of the values $F(x,y)$ and $R(x,y)$ assigned to the same picture point is formed and is stored—as the case may be after an additional processing step—in the memory 24 as output picture $A(x,y)$. Since the sound skin portions in the fluorescence picture and in the reference picture show at least approximately similar intensity variations, the output picture has for the associated picture points an at least approximately constant value, which lies below a value Ao indicated by a broken line in FIG. 2b. At the areas of the relative maxima F1, F2, on the contrary, maxima A1 and A2 are obtained, which are considerably larger than this value.

In the output picture produced in this manner and displayed on the monitor 3, the transitional region 30 between sound and sick tissue including the melanoma is brighter than the sound skin parties. However, the brightness differences can be so small that they are not immediately noticed by an observer. In this case, the contrast between sound tissue and the environmental region can be increased in a simple manner in that, for example, those values $A(x,y)$ which exceed the threshold value Ao are multiplied by a factor which is larger than unity, as a result of which the relevant picture points are displayed more brightly on the picture screen of the monitor or that the values are presented in a pseudo coloured form. Since the examination region can be comparatively extensive, for example 15×20 cm, it is possible to examine larger skin parties rapidly with respect to melanomae.

In the embodiment, three picture memories—for the fluorescence picture, the reference picture and the output picture—are provided, but two picture memories are sufficient, if, for example, in the memory 22 the picture $F(x,y)$ is replaced picture point for picture point by the picture $A(x,y)$ dependent upon the quotient $F(x,y)/R(x,y)$. If the quotient formation can be carded out on-line upon the arrival of the values $R(x,y)$, even only one picture memory is required.

In the foregoing, the method according to the invention has been described in connection with the diagnosis of melanomae. However, it is also possible to discover thereby other tumors at the surface of the human body, whose emission of fluorescence light differs from that of the sound tissue.

What is claimed is:

1. An apparatus for detecting anomalies of the skin comprising light illumination means for illuminating a two-dimensionally extending examination region of said skin, via a beam between said illuminating means and said examination region with light in an ultraviolet wavelength range during a first time interval and with light in a visible wavelength range during a second time interval different from said first time interval; a camera means for recording a fluorescence picture of fluorescent light from the examination region during the first time interval produced by said skin in response to said light in the ultraviolet wavelength range, said fluorescence picture having signal values F(x,y) at its picture points x,y and for recording a reference picture of the examination region during the second time interval in response to said light in the visible wavelength range, said reference picture having signal values R(x,y) at its picture points x,y during the second time interval; memory means for storing the signal values of at least one of the fluorescence picture and said reference picture; and processing means responsive to said memory means for producing an output picture having respective signal values A(x,y) at its picture points x,y which are formed from respective quotients F(x,y)/R(x,y) of the signal values of the fluorescence and reference pictures at the same picture points.

2. An apparatus as claimed in claim 1, wherein said light illumination means comprises at least one light source means for emitting light simultaneously in said ultraviolet and visible wavelength ranges via said beam path between said light illumination means and said examination region; a first filter selectively positionable in said beam path for transmitting light in said ultraviolet wavelength range while suppressing transmission of light in said visible wavelength range; and a second filter selectively positionable in said beam path between said light illumination means and said examination region for transmitting light in said visible wavelength range while suppressing transmission of light in said ultraviolet wavelength range.

3. An apparatus as claimed in claim 2 including a frosted pane present in said beam path.

4. An apparatus as claimed in claim 3 including a filter arranged before the camera means for suppressing light from the ultraviolet wavelength range while transmitting light from a wavelength range of the fluorescent light.

5. An apparatus as claimed in claim 4 including a filter arranged before the camera means for suppressing transmission of light from the ultraviolet wavelength range while transmitting light from the visible wavelength range.

6. An apparatus as claimed in claim 5 including polarization filters adapted for selective placement into a beam path between the camera means and the light illumination means, which polarization filters are shaped and arranged for suppressing any directed reflection in the reference picture produced by the camera.

7. An apparatus as claimed in claim 6 wherein the visible wavelength range is an isobestic range.

8. An apparatus as claimed in claim 5 wherein the visible wavelength range is an isobestic range.

9. An apparatus as claimed in claim 2 including a third filter arranged before the camera means for suppressing transmission of light from the ultraviolet wavelength range while transmitting light from the visible wavelength range.

10. An apparatus as claimed in claim 1 including a frosted pane present in said beam path.

11. An apparatus as claimed in claim 10 including a filter arranged before the camera means for suppressing transmission of light from the ultraviolet wavelength range while transmitting light from the visible wavelength range.

12. An apparatus as claimed in claim 10 wherein the visible wavelength range is an isobestic range.

13. An apparatus as claimed in claim 1 including a filter, arranged before the camera means, for suppressing light from the ultraviolet wavelength range while transmitting light from a wavelength range of the fluorescent light.

14. An apparatus as claimed in claim 13 wherein the visible wavelength range is an isobestic range.

15. An apparatus as claimed in claim 1 including a filter, arranged before the camera means, for suppressing transmission of light from the ultraviolet wavelength range while transmitting light from the visible wavelength range.

16. An apparatus as claimed in claim 15 including polarization filters adapted for selective placement into a beam path between the camera means and the light illumination means, which polarization filters are shaped and arranged for suppressing any directed reflection in the reference picture produced by the camera.

17. An apparatus as claimed in claim 1 including polarization filters adapted for selective placement into a beam path between the camera means and the light illumination means, which polarization filters are shaped and arranged for suppressing any directed reflection in the reference picture produced by the camera.

18. An apparatus as claimed in claim 17 wherein the visible wavelength range is an isobestic range.

19. An apparatus as claimed in claim 1 wherein the visible wavelength range is an isobestic range.

20. A method of detecting anomalies of the skin comprising illuminating a two-dimensionally extending examination region of said skin with light in an ultraviolet wavelength range during a first time interval; recording a fluorescence picture of fluorescent light from the examination region during said first time interval produced by said skin in response to said light in an ultraviolet light range, said fluorescence picture having signal values F(x,y) at its picture points x,y; illuminating the examination region with light in a visible wavelength range during a second time interval different from said first time interval; recording a reference picture during the second time interval in response to said light in the visible wavelength range, said reference picture having signal values R(x,y) at its picture points x,y; storing the signal values of at least one of the recorded fluorescence and reference pictures; and producing an output picture having signal values A(x,y) at its picture points x,y which is formed from respective quotients F(x,y)/R(x,y) of the signal values of the fluorescence and reference pictures at the same picture points.

21. A method as claimed in claim 1, wherein said illuminating with light in said ultraviolet wavelength range and said illuminating with light in said visible wavelength range each comprises emitting light from a source simultaneously in said ultraviolet and visible wavelength ranges via a beam path between said source and said examination region, said illuminating with light in said ultraviolet wavelength range further comprising imposing a first filter in said beam path between said source and said examination region for transmitting light in said ultraviolet wavelength range while suppressing transmission of light in said visible wavelength range and said illuminating with light of said second wavelength range further comprising imposing a second filter in said beam path between said source and said examination region for transmitting light in said visible wavelength range while suppressing transmission of light in said ultraviolet wavelength range.

* * * * *